(12) United States Patent
Hashimoto et al.

(10) Patent No.: US 8,518,125 B2
(45) Date of Patent: Aug. 27, 2013

(54) EMULSION DYEING COMPOSITION CONTAINING AT LEAST ONE PHOSPHOLIPID, AT LEAST ONE NONIONIC SURFACTANT AND AT LEAST ONE CARBOXYLIC ACID, AND METHOD OF USING SAME

(75) Inventors: Sawa Hashimoto, Garwood, NJ (US); Nghi Van Nguyen, Edison, NJ (US); Tan Siliu, Westfield, NJ (US)

(73) Assignee: L'Oreal, Paris (FR)

( * ) Notice: Subject to any disclaimer, the term of this patent is extended or adjusted under 35 U.S.C. 154(b) by 43 days.

(21) Appl. No.: 13/276,491

(22) Filed: Oct. 19, 2011

(65) Prior Publication Data

US 2012/0325260 A1    Dec. 27, 2012

Related U.S. Application Data

(63) Continuation of application No. 13/167,811, filed on Jun. 24, 2011, now abandoned.

(51) Int. Cl.
*A61Q 5/10* (2006.01)

(52) U.S. Cl.
USPC .......... 8/405; 8/406; 8/408; 8/410; 8/411; 8/412; 8/421; 8/435; 8/580; 8/609

(58) Field of Classification Search
USPC ............ 8/405, 406, 408, 410, 411, 412, 421, 8/435, 580, 609
See application file for complete search history.

(56) References Cited

U.S. PATENT DOCUMENTS

| | | | |
|---|---|---|---|
| 4,157,388 A | 6/1979 | Christiansen | |
| 4,702,906 A | 10/1987 | Jacquet et al. | |
| 4,719,282 A | 1/1988 | Nadolsky et al. | |
| 5,061,289 A | 10/1991 | Clausen et al. | |
| 5,380,340 A | 1/1995 | Neunhoeffer et al. | |
| 5,766,576 A | 6/1998 | Lowe et al. | |
| 5,961,667 A * | 10/1999 | Doehling et al. | 8/408 |
| 6,099,593 A | 8/2000 | Terranova et al. | |
| 6,270,533 B1 | 8/2001 | Genet et al. | |
| 6,338,741 B1 | 1/2002 | Vidal et al. | |
| 6,340,371 B1 | 1/2002 | Genet et al. | |
| 6,379,398 B1 | 4/2002 | Genet et al. | |
| 6,565,614 B1 | 5/2003 | Genet et al. | |
| 6,616,706 B1 | 9/2003 | Kahre et al. | |
| 6,638,321 B1 | 10/2003 | Genet et al. | |
| 6,645,258 B2 | 11/2003 | Vidal et al. | |
| 6,946,005 B2 | 9/2005 | Sabelle et al. | |
| 7,449,029 B2 | 11/2008 | Nguyen et al. | |
| 7,608,569 B2 | 10/2009 | Nguyen et al. | |
| 7,727,288 B2 | 6/2010 | Nguyen et al. | |
| 2003/0229949 A1 | 12/2003 | Sabelle et al. | |
| 2004/0194227 A9 | 10/2004 | Sabelle et al. | |
| 2006/0286055 A1 | 12/2006 | Cannell et al. | |
| 2006/0286056 A1 | 12/2006 | Cannell et al. | |
| 2006/0286057 A1 | 12/2006 | Cannell et al. | |
| 2006/0292100 A1 | 12/2006 | Nguyen et al. | |
| 2007/0110691 A1 | 5/2007 | Nguyen et al. | |
| 2008/0085253 A1 | 4/2008 | Nguyen et al. | |
| 2008/0085254 A1 | 4/2008 | Nguyen et al. | |
| 2008/0085255 A1 | 4/2008 | Nguyen et al. | |
| 2008/0085258 A1 | 4/2008 | Nguyen et al. | |
| 2008/0095725 A1 * | 4/2008 | Nguyen et al. | 424/70.7 |
| 2008/0095726 A1 | 4/2008 | Nguyen et al. | |
| 2008/0095727 A1 | 4/2008 | Nguyen et al. | |
| 2008/0095728 A1 | 4/2008 | Nguyen et al. | |
| 2008/0095729 A1 | 4/2008 | Nguyen et al. | |
| 2008/0096781 A1 | 4/2008 | Nguyen et al. | |
| 2008/0096782 A1 | 4/2008 | Nguyen et al. | |
| 2008/0097070 A1 | 4/2008 | Nguyen et al. | |
| 2009/0053161 A1 | 2/2009 | Nguyen et al. | |
| 2010/0154140 A1 * | 6/2010 | Simonet et al. | 8/416 |

FOREIGN PATENT DOCUMENTS

| | | |
|---|---|---|
| CA | 2280989 | 3/2000 |
| DE | 2359399 | 11/1973 |
| DE | 1486576 | 11/1974 |
| DE | 3843892 | 12/1988 |
| DE | 4133957 | 10/1991 |
| DE | 19543988 | 11/1995 |
| EP | 80976 | 11/1982 |
| EP | 122324 | 11/1983 |
| EP | 1348695 | 1/2003 |
| FR | A2733749 | 2/1932 |
| FR | A2750048 | 4/1932 |
| FR | 2766177 | 7/1997 |
| FR | 2766178 | 7/1997 |
| FR | 2766179 | 7/1997 |
| FR | 2782716 | 9/1998 |
| FR | 2782718 | 9/1998 |
| FR | 2782719 | 9/1998 |
| JP | 02019576 | 1/1990 |
| JP | 9110659 | 4/1997 |
| WO | 9408969 | 4/1994 |
| WO | 9408970 | 4/1994 |
| WO | 9615765 | 11/1995 |

OTHER PUBLICATIONS

McCutcheon's "Detergent and Emulsifiers", North American Edition (1986), published by Allured Publishing Corporation.

(Continued)

*Primary Examiner* — Eisa Elhilo

(74) *Attorney, Agent, or Firm* — L'Oreal USA

(57) ABSTRACT

The present invention is drawn to a composition and method for dyeing keratinous substrates containing: (a) at least one phospholipid; (b) at least one nonionic surfactant; (c) at least one compound chosen from an alkyl ether carboxylic acid, an alkyl ether carboxylate, a fatty acid having from about 6 to about 40 carbon atoms, and mixtures thereof; (d) at least one dye chosen from oxidation dye precursors and direct dyes. The compositions of the present invention may optionally contain at least one thickening agent, at least one alkaline agent, at least one fatty substance other than a fatty acid, at least one salt, and at least one oxidizing agent.

46 Claims, No Drawings

(56) References Cited

OTHER PUBLICATIONS

McCutcheon's "Functional Materials", North American Edition (1992).
International Cosmetic Ingredient Dictionary and Handbook, 8th Edition, vol. 2 (2000), published by the Cosmetic, Toiletry and Fragrance Association Inc. (CTFA)—pp. 1701 to 1703.
International Cosmetic Ingredient Dictionary and Handbook, 7th Edition, published by the Cosmetic, Toiletry and Fragrance Association Inc. (CTFA), (1997).
International Cosmetic Ingredient Dictionary and Handbook, 10th Edition, published by the Cosmetic, Toiletry and Fragrance Association Inc. (CTFA), (2004).
Walter Noll "Chemistry and Technology of Silicones" (1968), Academic Press.
Cosmetic and Toiletries, vol. 91, Jan. 1976, pp. 29 to 32—Todd Byers "Volatile Silicone Fluids for Cosmetics".
CARODA, "Croda Personal Care: product finder", Mar. 2013, http://www.croda.com.

* cited by examiner

EMULSION DYEING COMPOSITION CONTAINING AT LEAST ONE PHOSPHOLIPID, AT LEAST ONE NONIONIC SURFACTANT AND AT LEAST ONE CARBOXYLIC ACID, AND METHOD OF USING SAME

CROSS-REFERENCE TO RELATED APPLICATION

This application claims the benefit of the filing date of U.S. Non-Provisional application Ser. No. 13/167,811, filed Jun. 24, 2011, the contents of which are incorporated by reference.

STATEMENT OF RELATED APPLICATIONS

Not applicable.

BACKGROUND OF THE INVENTION

Throughout the years, people have sought to modify the color of their skin, their eyelashes or their hair. Several techniques have been developed to achieve the desired color.

It is known to dye human keratinous substrates, such as the hair, with dye compositions comprising oxidation dye precursors, which are also known as oxidation bases. To vary the shades obtained with these oxidation bases, additional couplers or coloration modifiers may be employed.

It is also known to dye human keratinous substrates by direct dyeing, which comprises applying to the keratinous substrates direct dyes, which are colored.

Traditional application time for dyeing keratinous substrates is around thirty minutes. Such a period is considered to be too long under current tendency.

This problem cannot be solved by merely reducing the application time of the dyeing compositions since it would be difficult to maintain the same satisfactory levels of coloring in shortened application times.

Another way to solve the problem is to increase the power of the oxidizing agent and the alkaline agent, by employing, for example, oxidizing agents of the type of the persalts, and/or alternatively by increasing the pH of the dyeing composition. However, such an option is undesirable, because of the increased risk of degradation of the keratinous substrates.

Therefore, there is a real need to develop dyeing compositions with improved efficiency to yield minimum degradation of the treated keratinous substrates while achieving improved levels of coloring in both conventional application time e.g., around 30 minutes and in shortened application times, e.g., around 15 minutes.

Another object of the present invention is to provide an effective dyeing composition capable of depositing acceptable levels of color onto keratinous substrates utilizing decreased levels of dye therein.

It is also desirable that such a composition can provide other advantageous properties to the hair such as shine, conditioning and a healthy appearance.

Finally, it is an object of the present invention to provide an effective dyeing composition with lowered cost of production.

BRIEF SUMMARY OF THE INVENTION

In order to achieve these and other advantages, the present invention is drawn to a ready-to-use aqueous composition for dyeing keratinous substrates containing, in a cosmetically acceptable medium:

a) at least one phospholipid;
b) at least one nonionic surfactant;
c) at least one compound chosen from an alkyl ether carboxylic acid, an alkyl ether carboxylate, a fatty acid having from about 6 to about 40 carbon atoms, and mixtures thereof; and
d) at least one dye chosen from oxidation dye precursors and direct dyes;
e) optionally, at least one thickening agent;
f) optionally, at least one alkaline agent;
g) optionally, at least one fatty substance other than a fatty acid;
h) optionally, at least one salt; and
i) optionally, at least one oxidizing agent.

In another embodiment, the present invention is drawn to a method for dyeing a keratinous substrate comprising contacting the keratinous substrate with a ready-to-use aqueous composition containing, in a cosmetically acceptable medium:

a) at least one phospholipid;
b) at least one nonionic surfactant;
c) at least one compound chosen from an alkyl ether carboxylic acid, an alkyl ether carboxylate, a fatty acid having from about 6 to about 40 carbon atoms, and mixtures thereof; and
d) at least one dye chosen from oxidation dye precursors and direct dyes;
e) optionally, at least one thickening agent;
f) optionally, at least one alkaline agent;
g) optionally, at least one fatty substance other than a fatty acid;
h) optionally, at least one salt; and
i) optionally, at least one oxidizing agent.

According to another embodiment of the invention, a kit for dyeing keratinous substrates is provided, comprising:

a first unit containing in a cosmetically acceptable medium: at least one phospholipid; at least one nonionic surfactant; at least one compound chosen from an alkyl ether carboxylic acid, an alkyl ether carboxylate, a fatty acid having from about 6 to about 40 carbon atoms, and mixtures thereof; and at least one dye chosen from oxidation dye precursors and direct dyes; optionally, at least one thickening agent; optionally, at least one alkaline agent; optionally, at least one fatty substance other than a fatty acid; and optionally, at least one salt; and a second unit comprising at least one oxidizing agent and optionally, at least one fatty substance other than a fatty acid.

DETAILED DESCRIPTION OF THE INVENTION

Other than in the operating examples, or where otherwise indicated, all numbers expressing quantities of ingredients and/or reaction conditions are to be understood as being modified in all instances by the term "about" which encompasses ±10%.

"At least one" as used herein means one or more and thus includes individual components as well as mixtures/combinations.

"Conditioning" as used herein means imparting to at least one keratinous fiber at least one property chosen from combability, manageability, moisture-retentivity, luster, shine, and softness. The state of conditioning is evaluated by measuring, and comparing, the ease of combability of the treated hair and of the untreated hair in terms of combing work (gm-in).

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii).

Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups.

The substituent(s) may be further substituted.

"Ethylene oxide group" as defined herein refers to a group of formula —$CH_2CH_2$—O—.

"Propylene oxide group" as defined herein includes groups of formula —$CH_2CH_2CH_2$—O—, groups of formula $(CH_3)CHCH_2$—O—, and groups of formula —$CH_2$ $(CH_3)CH$—O—.

"Keratinous substrate" may be chosen from, for example, hair, eyelashes, and eyebrows, as well as the stratum corneum of the skin and nails.

"Polymers," as defined herein, include homopolymers and copolymers formed from at least two different types of monomers.

The present invention provides for the use of conventional organic phospholipids. Particularly preferred organic phospholipids include lecithins. Lecithins are mixtures of phospholipids, i.e., diglycerides of fatty acids linked to an ester of phosphoric acid. Preferably, lecithins are diglycerides of stearic, palmitic, and oleic acids linked to the choline ester of phosphoric acid. Lecithin is usually defined either as pure phosphatidyl cholines or as crude mixtures of phospholipids which include phosphatidyl choline, phosphatidyl serine, phosphatidyl ethanolamine, phosphatidyl inositol, other phospholipids, and a variety of other compounds such as fatty acids, triglycerides, sterols, carbohydrates, and glycolipids.

The lecithin used in the present invention may be present in the form of a liquid, powder, or granules. Lecithins useful in the invention include, but are not limited to, soy lecithin and hydroxylated lecithin. For example, ALCOLEC S is a fluid soy lecithin, ALCOLEC F 100 is a powder soy lecithin, and ALCOLEC Z3 is a hydroxylated lecithin, all of which are available from the American Lecithin Company.

Other than lecithins, additional examples of phospholipids which may be useful in the present invention include, but are not limited to, multifunctional biomimetic phospholipids. For example, the following multifunctional biomimetic phospholipids manufactured by Uniqema Industries may be useful: PHOSPHOLIPID PTC, PHOSPHOLIPID CDM, PHOSPHOLIPID SV, PHOSPHOLIPID GLA, and PHOSPHOLIPID EFA (linoleamidopropyl PG-dimonium chloride phosphate).

In the present invention, the at least one phospholipid is preferably used in an amount of from greater than 0% to about 20% by weight, preferably from about 0.01% to about 10% by weight, and more preferably from about 0.1% to about 5% by weight, and even more preferably from about 1% to about 4% by weight, based on the weight of the composition as a whole.

Nonionic Surfactants

In general, nonionic surfactants having a Hydrophilic-Lipophilic Balance (HLB) of from 8 to 20 are contemplated for use by the present invention. Nonlimiting examples of nonionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, preferably in the $C_{16}$-$C_{40}$ range, more preferably in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Uniqema, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula $(S)_n$—O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use herein are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20).

Preferred nonionic surfactants are those formed from a fatty alcohol, a fatty acid, or a glyceride with a $C_4$ to $C_{36}$ carbon chain, preferably a $C_{12}$ to $C_{18}$ carbon chain, more preferably a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably at least 8. Preferably the nonionic surfactants contain ethoxylate in a molar content of from about 10-25, more preferably from about 10-20 moles.

The nonionic surfactant will typically be present in the composition in an amount of from greater than 0% to about 70% by weight, preferably from about 0.1 to 50% by weight, and more preferably from about 1 to about 30% by weight, and more preferably from greater than 5% to about 20% by weight, based on the total weight of the composition.

The alkyl ether carboxylic acid or alkyl ether carboxylate used in the present invention corresponds to formula I:

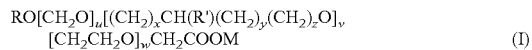
$$RO[CH_2O]_u[(CH_2)_xCH(R')(CH_2)_y(CH_2)_zO]_v[CH_2CH_2O]_wCH_2COOM \qquad (I)$$

wherein:
R is a hydrocarbon radical containing from 6 to 40 carbon atoms;
u, v and w, independently of one another, represent numbers of from 0 to 60;
x, y and z, independently of one another, represent numbers of from 0 to 13;
R' represents hydrogen, alkyl, the sum of x+y+z being $\geq 0$;
M is an alkali metal or alkaline earth metal (i.e., ether carboxylate) or hydrogen (i.e., ether carboxylic acid).

Ether carboxylic acids or carboxylates corresponding to formula (I) can be obtained by alkoxylation of alcohols ROH with ethylene oxide as sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (I), R is linear or branched, acyclic or cyclic, saturated or unsaturated, aliphatic or aromatic, substituted or unsubstituted, preferably a linear or branched, acyclic $C_{6-40}$ alkyl or alkenyl group or a $C_{1-40}$ alkyl phenyl group, more particularly a $C_8$-$C_{22}$ alkyl or alkenyl group or a $C_4$-$C_{18}$ alkyl phenyl group, more preferably a $C_{12}$-$C_{18}$ alkyl group or alkenyl group or a $C_6$-$C_{16}$ alkyl phenyl group;
u, v, w, independently of one another, is preferably a number from 2 to 20, more preferably a number from 3 to 17 and most preferably a number from 5 to 15;
x, y, z, independently of one another, is preferably a number from 2 to 13, more preferably a number from 1 to 10 and most preferably a number from 0 to 8;
M may be chosen from lithium, sodium, potassium, calcium, magnesium or hydrogen.

Suitable ether carboxylic acids or ether carboxylates include, but are not limited to, the following representatives referred to by their INCI names (INCI: nomenclature for raw materials according to the International Cosmetic Ingredient Dictionary, 7th Edition, published by the Cosmetic, Toiletry and Fragrance Association Inc. (CTFA), Washington D.C., USA): Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, $C_{11}$-$C_{15}$ Pareth-7 Carboxylic Acid, $C_{12}$-$C_{13}$ Pareth-5 Carboxylic Acid, $C_{12}$-$C_{13}$ Pareth-8 Carboxylic Acid, C12-13 Pareth-12 Carboxylic Acid, $C_{12}$-$C_{15}$ Pareth-7 Carboxylic Acid, $C_{12}$-$C_{15}$ Pareth-8 Carboxylic Acid, $C_{14}$-$C_{15}$ Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, Magnesium Laureth-11 Carboxylate, Sodium-PPG-6-Laureth-6-Carboxylate, Sodium PPG-8-Steareth-7 Carboxylate, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Sodium Capryleth-2 Carboxylate, Sodium Capryleth-9 Carboxylate, Sodium Ceteth-13 Carboxylate, Sodium C9-11 Pareth-6 Carboxylate, Sodium $C_{11}$-$C_{15}$ Pareth-7 Carboxylate, Sodium $C_{12}$-$C_{13}$ Pareth-5 Carboxylate, Sodium $C_{12}$-$C_{13}$ Pareth-8 Carboxylate, Sodium $C_{12}$-$C_{13}$ Pareth-12 Carboxylate, Sodium $C_{12}$-$C_{15}$ Pareth-6 Carboxylate, Sodium $C_{12}$-$C_{15}$ Pareth-7 Carboxylate, Sodium $C_{12}$-$C_{15}$ Pareth-8 Carboxylate, Sodium $C_{14}$-$C_{15}$ Pareth-8 Carboxylate, Sodium Deceth-2 Carboxylate, Sodium Hexeth-4 Carboxylate, Sodium Isosteareth-6 Carboxylate, Sodium Isosteareth-11 Carboxylate, Sodium Laureth-3 Carboxylate, Sodium Laureth4 Carboxylate, Sodium Laureth-5 Carboxylate, Sodium Laureth-6 Carboxylate, Sodium Laureth-8 Carboxylate Sodium Laureth-11 Carboxylate, Sodium Laureth-12 Carboxylate, Sodium Laureth-13 Carboxylate, Sodium Laureth-14 Carboxylate, Sodium Laureth-17 Carboxylate, Sodium Trudeceth-3 Carboxylate, Sodium Trideceth-6 Carboxylate, Sodium Trideceth-7 Carboxylate, Sodium Trideceth-8 Carboxylate, Sodium Trideceth-12 Carboxylate, Sodium Undeceth-5 Carboxylate, Trideceth-3 Carboxylic Acid, Trideceth4 Carboxylic Acid, Trideceth-7 Carboxylic acid, Trideceth-15 Carboxylic Acid, Trideceth-19 Carboxylic Acid, Undeceth-5 Carboxylic Acid.

Particularly preferred are oleth-10 carboxylic acid, laureth-5 carboxylic acid, and laureth-11 carboxylic acid.

The fatty acid having from about 6 to about 40 carbon atoms that may also be used in the present invention corresponds to formula II:

$$R'''COOH \qquad (II)$$

wherein:
R'''' is a hydrocarbon radical containing from 6 to 40 carbon atoms. In addition, R'''' is linear or branched, acyclic or cyclic, saturated or unsaturated, aliphatic or aromatic, substituted or unsubstituted, preferably a linear or branched, acyclic $C_{6-40}$ alkyl or alkenyl group or a $C_{1-40}$ alkyl phenyl group, more particularly a $C_{8-22}$ alkyl or alkenyl group or a $C_{4-18}$ alkyl phenyl group, more preferably a $C_{12-18}$ alkyl group or alkenyl group or a $C_{6-16}$ alkyl phenyl group.

Suitable fatty acids having from about 6 to about 40 carbon atoms include, but are not limited to the following representatives referred to by their INCI names (INCI: nomenclature for raw materials according to the International Cosmetic Ingredient Dictionary, 10th Edition, published by the Cosmetic, Toiletry and Fragrance Association Inc. (CTFA), Washington D.C., USA): Arachidic Acid, Arachidonic Acid, Beeswax Acid, Capric Acid, Caproic Acid, Caprylic Acid, Coconut Acid, Isostearic Acid, Lauric Acid, Linoleic Acid, Linolenic Acid, Myristic Acid, Oleic Acid, Olive Acid, Palmitic Acid, Rapeseed Acid, Stearic Acid, Tallow Acid, Undecanoic Acid, Undecylenic Acid, Wheat Germ Acid.

Particularly preferred fatty acids having from about 6 to about 40 carbon atoms include Capric Acid, Caprylic Acid, Lauric Acid, Linoleic Acid, Oleic Acid, Isostearic Acid, and Stearic Acid.

The alkyl ether carboxylic acid and/or alkyl ether carboxylate and/or fatty acid having from about 6 to about 40 carbon atoms is present in the composition in an amount ranging from greater than 0 to about 40% by weight, preferably from about 0.1 to about 30% by weight, and more preferably from about 0.5 to about 20% by weight, and even more preferably from about 2 to about 10% by weight, based on the weight of the composition as a whole.

Dye Compounds

The dye compounds of the present disclosure may be chosen from oxidation bases, couplers, and direct dyes.

Oxidation Bases

Examples of oxidation bases include ortho or para aminophenols, ortho or para phenylenediamines, double bases, heterocyclic bases, and the acid addition salts thereof.

The para-phenylenediamines which can be used include compounds of the following formula (A) and their addition salts with an acid:

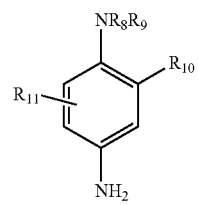

(A)

in which:

$R_8$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical, a $C_1$-$C_4$ alkyl radical substituted by a nitrogenous group, a phenyl radical or a 4'-aminophenyl radical;

$R_9$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical or a $C_1$-$C_4$ radical substituted by a nitrogenous group;

$R_8$ and $R_9$ can also form, with the nitrogen atom which carries them, a 5- or 6-membered nitrogenous heterocycle optionally substituted by one or more alkyl, hydroxyl or ureido groups;

$R_{10}$ represents a hydrogen atom, a halogen atom, such as a chlorine atom, a $C_1$-$C_4$ alkyl radical, a sulpho radical, a carboxyl radical, a $C_1$-$C_4$ monohydroxyalkyl radical, a $C_1$-$C_4$ hydroxyalkoxy radical, a $C_1$-$C_4$ acetylaminoalkoxy radical, a $C_1$-$C_4$ mesylaminoalkoxy radical or $C_1$-$C_4$ carbamoylaminoalkoxy radicals;

$R_{11}$ represents a hydrogen atom, a halogen atom or a $C_1$-$C_4$ alkyl radical.

The nitrogenous groups in the above formula (A) include amino, mono($C_1$-$C_4$)alkylamino, di($C_1$-$C_4$)alkylamino, tri ($C_1$-$C_4$)alkylamino, monohydroxy($C_1$-$C_4$)alkylamino, imidazolinium and ammonium radicals.

The para-phenylenediamines of above formula (A) include para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-methyl-1-N-(β-hydroxyethyl)-para-phenylenediamine and their addition salts with an acid.

In one embodiment, the para-phenylenediamines of above formula (A) include para-phenylenediamine, para-toluoylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and their addition salts with an acid.

The ortho-phenylenediamines include N1-(2-hydroxyethyl)-4-nitro-o-phenylenediamine, 4-methyl-o-phenylenediamine, and 4-nitro-o-phenylenediamine and acid addition salts thereof.

As used herein, the term "double bases" means compounds comprising at least two aromatic nuclei having at least one of amino and hydroxyl groups.

Examples include compounds corresponding to the following formula (B) and their addition salts with an acid:

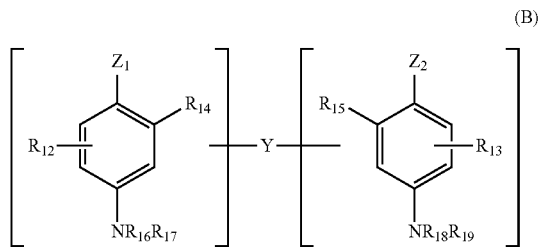

(B)

in which:

$Z_1$ and $Z_2$, which are identical or different, represent a hydroxyl or —$NH_2$ radical which can be substituted by a $C_1$-$C_4$ alkyl radical or by a connecting arm Y;

the connecting arm Y represents a linear or branched alkylene chain comprising from 1 to 14 carbon atoms which can be interrupted or terminated by one or more nitrogenous groups and/or by one or more heteroatoms, such as oxygen, sulphur or nitrogen atoms, and which is optionally substituted by one or more hydroxyl or $C_1$-$C_6$ alkoxy radicals;

$R_{12}$ and $R_{13}$ represent a hydrogen or halogen atom, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical or a connecting arm Y;

$R_{14}$, $R_{15}$, $R_{16}$, $R_{17}$, $R_{18}$ and $R_{19}$, which are identical or different, represent a hydrogen atom, a connecting arm Y or a $C_1$-$C_4$ alkyl radical;

it is being understood that the compounds of formula (B) only comprise a single connecting arm Y per molecule.

Nitrogenous groups of the above formula (B) include amino, mono($C_1$-$C_4$)alkylamino, di($C_1$-$C_4$)alkylamino, tri ($C_1$-$C_4$)alkylamino, monohydroxy($C_1$-$C_4$)alkylamino, imidazolinium and ammonium radicals.

Additional examples of double bases of above formula (B) include of N,N'-bis(β-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine, 1,8-bis(2,5-diaminophenoxy)-3,5-dioxaoctane and their addition salts with an acid.

In one embodiment the double base is N,N'-Bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid.

The para-aminophenols which can be used include compounds of the following formula (C) and their addition salts with an acid:

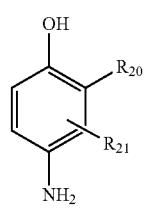

(C)

in which:

$R_{20}$ represents a hydrogen atom, a halogen atom, such as fluorine, a $C_1$-$C_4$ alkyl radical, a $C_1$-$C_4$ monohydroxyalkyl radical, a ($C_1$-$C_4$)alkoxy($C_1$-$C_4$) alkyl radical, a $C_1$-$C_4$ aminoalkyl radical or a hydroxy($C_1$-$C_4$)alkylamino-($C_1$-$C_4$)alkyl radical, $R_{21}$ represents a hydrogen atom, a halogen atom, such as fluorine, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical, a $C_1$-$C_4$ cyanoalkyl radical or a ($C_1$-$C_4$) alkoxy($C_1$-$C_4$)alkyl radical.

Among the para-aminophenols, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, N-methyl-para-aminophenol, and the acid addition salts thereof.

The ortho-aminophenols that may be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Heterocyclic bases that can be used as oxidation bases in the methods of coloring keratinous substrates include pyridine derivatives, pyrimidine derivatives, pyrazole derivatives, pyrazolinone derivatives, and the acid addition salts thereof.

Pyridine derivatives include the compounds described, for example, in patents GB 1,026,978 and GB 1,153,196, as well as the compounds 2,5-diaminopyridine, 2-(4-methoxyphenyl)amino-3-aminopyridine, 2,3-diamino-6-methoxypyridine, 2-(β-methoxyethyl)amino-3-amino-6 methoxypyridine, 3,4-diaminopyridine, and the acid addition salts thereof.

Pyrimidine derivatives include the compounds disclosed, for example, in German Patent DE 2 359 399 or Japanese Patents JP 88-169 571 and JP 91-10659 or Patent Application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives, such as those mentioned in French Application FR-A-2 750 048 and among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethyl-pyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-(imidazolylpropylamino)pyrazolo[1,5-a]pyrimidine; and their addition salts and their tautomeric forms, when there exists a tautomeric equilibrium, and their addition salts with an acid.

Pyrazole and pyrazolinone derivatives include the compounds described in patents DE 3,843,892, DE 4,133,957 and patent applications WO 94/08969, WO 94/08970, FR-A-2, 733,749, and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, 2-(4,5-diamino-1H-pyrazol-1-yl), $H_2SO_4$, 2,3-diamino-6,7-dihydro-1H,5H-pyrazolo[1,2-z]pyrazol-1-one, 1-methyl-3-phenyl-2-pyrazolinone, and the acid addition salts thereof.

Even further non-limiting mentions can be made of 2,3-diamino-6,7-dihydro-1H,5H-pyrazolo[1,2-a]pyrazol-1-one and/or addition salts thereof.

As heterocyclic bases, further non-limiting mentions can be made of 4,5-diamino-1-(β-hydroxyethyl) pyrazole and/or 2,3-diamino-6,7-dihydro-1H,5H-pyrazolo[1,2-a]pyrazol-1-one and/or addition salts thereof.

As cationic oxidation bases usable in the ready-to-use compositions according to the disclosure, non-limiting mentions can be made of the following compounds: the para-phenylenediamines for example as described in French Patent Application Nos. 2 766 177 and 2 766 178, the para-aminophenols as described for example in French Patent Application Nos. 2 766 177 and 2 766 178, the ortho-phenylenediamines as described for example in French Patent Application Nos. 2 782 718, 2 782 716 and 2 782 719, the ortho-aminophenols or cationic double bases such as derivatives of the bis(aminophenyl)alkylenediamine type described in French Patent Application No. 2 766 179, as well as the cationic heterocyclic bases, the compounds bearing at least one quaternary nitrogen atom.

For example, the cationic oxidation bases usable in the compositions according to the disclosure are cationic para-phenylenediamines. For example, in some embodiments cationic oxidation bases of para-phenylenediamine structure can be used, wherein at least one of the amine functions is a tertiary amine bearing a pyrrolidine nucleus, the molecule possessing at least one quaternized nitrogen atom. Such bases are described, for example, in European Patent Application Publication No. 1 348 695.

The oxidation bases may be employed in amounts ranging from 0.0001% to 12% by weight, or from 0.1% to 8.0% by weight, or from 1% to 5% by weight, based on the total weight of the composition.

Coupler Compounds

The compositions of the present disclosure may also contain coupler compounds. The couplers that may be used in the dyeing method disclosed herein include those conventionally used in oxidative methods of coloring keratinous fibers, for example, meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and the acid addition salts thereof.

Suitable color couplers include, for example, those having the general formula (D):

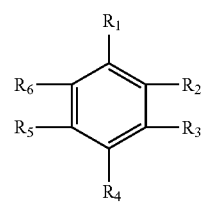

(D)

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(β-hydroxyethyl)amino]benzene, 1-methoxy-2-amino-4-[(β-hydroxyethyl)amino]benzene, 1-hydroxy-3-(dimethylamino)benzene, 6-methyl-1-hydroxy-3[(β-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(β-hydroxyethyl)amino-3-aminobenzene, 2-methyl-1,3-diaminobenzene, 6-methoxy-1-amino-3-[(β-hydroxyethyl)amino]-benzene, 6-(β-aminoethoxy)-1,3-diaminobenzene, 6-(β-hydroxyethoxy)-1-amino-3-

(methylamino)benzene, 6-carboxymethoxy-1,3-diaminobenzene, 6-ethoxy-1-bis(β-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Other couplers may be chosen, for example, from 2,4-diamino-1-β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino 1-(α-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, 6-methylpyrazolo[1,5-a]-benzimidazole, and the acid addition salts thereof.

In one embodiment, the couplers include resorcinol, 1-naphthol, 2-methylresorcinol, 4-amino-2-hydroxy toluene, m-aminophenol, 2,4-diaminophenoxyethanol, phenyl methyl pyrazolone, hydroxybenzomorpholine, 2-methyl-5-hydroxyetyylaminophenol, 6-hydroxyindole, 2-amino-3-hydroxypyridine, 5-amino-6-chloro-o-cresol, 4-chlororesorcinol, their salts, and mixtures thereof.

When they are present, couplers may be present in amounts ranging from 0.0001% to 12% by weight; or from 0.1% to 8% by weight; or from 1% to about 5% based on the total weight of the composition.

In general, the acid addition salts of the oxidation bases and couplers may be chosen from hydrochlorides, hydrobromides, sulphates, tartrates, lactates, and acetates.

Direct Dyes

A direct dye is a colored substance that does not require the use of an oxidizing agent in order to reveal its color. Suitable direct dyes which may be used according to the present invention may be chosen from acidic (anionic), basic (cationic), and neutral dyes.

"Acidic dye" is generally intended to mean a dye containing at least one COOH, $SO_3H$, $PO_3H$, or $PO_4H_2$ group, it being possible for said groups to exist in the form of salts. "Salts" is generally intended to mean salts of metals (for example, alkali metals or alkaline earth metals), salts of an organic amine that is optionally hydroxylated. Such dyes are also referred to as anionic dyes.

The acidic dyes that can be used in the context of this invention can be chosen from acidic nitro dyes, acidic azo dyes, acidic azine dyes, acidic triarylmethane dyes, acidic quinone dyes, acidic indo-amine dyes and acidic natural dyes, and mixtures thereof.

"Basic dyes" is generally intended to mean a dye that has at least one group bearing a positive charge, such as an ammonium group or a quaternized nitrogen atom in a ring. Such dyes are also referred to as cationic dyes.

The basic dyes that can be used in the context of this invention can be chosen from nitrobenzene dyes, azo dyes, azomethine dyes, methine dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylamethane-derived dyes and basic natural dyes, and mixtures thereof.

Preferably, the direct dyes may be present in amounts ranging from 0.001% to 30% by weight, preferably from 0.01% to 20% by weight, more preferably from 0.1% to 10% by weight, and even more preferably from 1% to 5% by weight, based on the total weight of the composition.

Thickening Agent

Thickening agents of the present invention may be chosen from polymeric thickeners and non-polymeric thickeners as described in US2010154140A, herein incorporated by reference in its entirety.

Thickening agents of the present invention may be chosen from polymeric thickeners and non-polymeric thickeners. The at least one polymeric thickener can be ionic or non-ionic, associative or non-associative polymer. Exemplary polymeric thickeners include various native gums. Representative non-polymeric thickening agents include mineral salts such as sodium chloride; oxyethylenated molecules and especially ethoxylated alkyl or acyl derivatives of polyols. These polymers can be modified physically or chemically.

In the present invention, the at least one thickening agent is preferably used in an amount of from greater than 0% to about 15% by weight, preferably about 0.1% to about 10% by weight, and more preferably from about 0.5% to about 5% by weight, and even more preferably from about 1% to about 4% by weight, based on the total weight of the composition.

Alkaline Agents

The at least one alkaline agent of the present invention may be chosen from organic amines, organic amine salts, ammonium salts, and inorganic bases.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched $C_1$-$C_8$ alkyl groups bearing at least one hydroxyl radical.

Organic amines may also be chosen from alkanolamines such as mono-, di- or trialkanolamines, comprising one to three identical or different $C_1$-$C_4$ hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, and tris(hydroxymethylamino)methane.

The organic amines correspond to formula III:

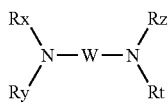

wherein W is chosen from $C_1$-$C_6$ alkylene residues optionally substituted with a hydroxyl group or a $C_1$-$C_6$ alkyl radical; Rx, Ry, Rz and Rt, which may be identical or different, are chosen from a hydrogen atom, $C_1$-$C_6$ alkyl radicals, $C_1$-$C_6$ hydroxyalkyl radicals, and $C_1$-$C_6$ aminoalkyl radicals.

Examples of such amines that may be mentioned include but not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Further as non-limiting examples, the amino acids may be chosen from basic amino acids comprising an additional amine function optionally included in a ring or in a ureido function.

Such basic amino acids may be chosen from those corresponding to formula (E) below:

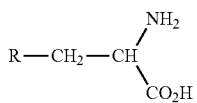

wherein R is a group chosen from:

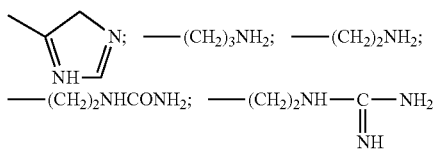

The compounds corresponding to formula (E) may be chosen from histidine, lysine, arginine, ornithine, and citrulline.

Amino acids that may be used in the present disclosure include but not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

In some embodiments, the organic amines are chosen from basic amino acids. The amino acids may be chosen from, for instance, arginine, lysine and histidine, or mixtures thereof.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

As a non-limiting example, the organic amines are chosen from alkanolamines. For example, the organic amines are chosen from 2-amino-2-methyl-1-propanol and monoethanolamine, or mixtures thereof. Further as an example, the organic amine is monoethanolamine.

The alkaline agent may be an organic amine in salt form. The term "organic amine salt," as used herein, means organic or mineral salts of an organic amine as described above.

As a non-limiting example, the organic salts may be chosen from the salts of organic acids, such as citrates, lactates, glycolates, gluconates, acetates, propionates, fumarates, oxalates and tartrates.

Further as a non-limiting example, the mineral salts may be chosen from hydrohalides (for example hydrochlorides), carbonates, hydrogen carbonates, sulfates, hydrogen phosphates, and phosphates.

The ammonium salts that may be used in the composition according to the present disclosure may be chosen from the following acid salts: carbonate, bicarbonate. For instance, the salt is the carbonate, such as ammonium carbonate.

The inorganic bases that may be used in the composition according to the present disclosure may be chosen from alkali metal phosphates and carbonates such as, for example, sodium phosphate, potassium phosphate, sodium carbonate, sodium bicarbonate, potassium carbonate, potassium bicarbonate, and their derivatives.

The inorganic bases may also include alkali metals of carboxylates such as, for example, sodium acetate, potassium acetate, sodium citrate, and potassium citrate, and their derivatives.

According to one embodiment, the ready-to-use composition of the present invention comprises an alkaline agent chosen from at least one organic amine such as at least one alkanolamine. When the composition comprises more than one alkaline agents including an alkanolamine and ammoniumhydroxides or salts thereof, the amount of organic amine(s) are for example higher than the amount of ammonia.

According to another embodiment, the ready-to-use composition of the present invention is substantially free of ammonia. The term "substantially free of ammonia" means that the composition of the present invention is either completely free of ammonia (including ammonium ions) or contains no appreciable amount of ammonia (including ammonium ions), for example, no more than 1% by weight, or no more than 0.5% by weight, or no more than 0.3% by weight, or no more than 0.1% by weight, based on the weight of the composition. According to this embodiment, the ready-to-use composition, for example, contains at least one alkanolamine such as monoethanolamine.

The at least one alkaline agent may be employed in the composition of the present invention in an amount ranging from about 0.001% to about 30% by weight, such as from about 0.01% to about 20% by weight or from about 0.1 to about 15% by weight, or from about 1 to about 10% by weight, based on the total weight of the composition.

Fatty Substance

The composition of the present invention may further comprise at least one fatty substance other than a fatty acid.

"Fatty substance" means an organic compound insoluble in water at normal temperature (25° C.) and at atmospheric pressure (760 mmHg) (solubility below 5% and such as below 1% and further such as below 0.1%). Fatty substances have in their structure a chain of at least two siloxane groups or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

The composition of the present invention comprises at least 10% of fatty substances by weight relative to the total weight of the composition, these substances being other than fatty acid.

Fatty substances are, for example, chosen from lower alkanes, fatty alcohols, esters of fatty acid, esters of fatty alcohol, oils such as mineral, vegetable, animal and synthetic non-silicone oils, non-silicone waxes and silicones.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the lower alkanes, in some embodiments, these have from 6 to 16 carbon atoms and are linear or branched, optionally cyclic. As examples, alkanes can be chosen from hexane and dodecane, isoparaffins such as isohexadecane and isodecane.

Non-limiting examples of non-silicone oils usable in the composition of the disclosure, include: hydrocarbon oils of animal origin, such as perhydrosqualene; hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam®. fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; nonafluoro-methoxybutane and nonafluoroethoxyisobutane; derivatives of perfluoromorpholine, such as 4-trifluoromethyl perfluoromorpholine sold under the name "PF 5052®" by the 3M Company.

The fatty alcohols usable as fatty substances in the composition of the disclosure include, but are not limited to, non-alkoxylated, saturated or unsaturated, linear or branched, and have from 6 to 30 carbon atoms and more particularly from to 30 carbon atoms; For example, cetyl alcohol, stearyl alcohol and their mixture (cetylstearyl alcohol), octyldodecanol, 2-butyloctanol, 2-hexyldecanol, 2-undecylpentadecanol, oleic alcohol or linoleic alcohol.

The exemplary non-silicone wax or waxes that can be used in the composition of the disclosure are chosen from carnauba wax, candelilla wax, and Alfa wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (cerabellina); other waxes or waxy raw materials usable according to the disclosure are, for example, marine waxes such as that sold by the company SOPHIM under reference M82, waxes of polyethylene or of polyolefins in general.

The exemplary fatty acid esters are the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting mentions of esters can be made of the esters of $C_4$-$C_{22}$ di- or tricarboxylic acids and of $C_1$-$C_{22}$ alcohols and the esters of mono-, di- or tricarboxylic acids and of $C_2$-$C_{26}$ di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The composition can also comprise, as fatty ester, esters and di-esters of sugars of $C_6$-$C_{30}$, such as $C_{12}$-$C_{22}$ fatty acids. "Sugar" as used in the disclosure means oxygen-containing hydrocarbon compounds that possess several alcohol functions, with or without aldehyde or ketone functions, and having at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives such as methylglucose.

The esters of sugars and of fatty acids can, for example, be chosen from the esters or mixtures of esters of sugars described previously and of linear or branched, saturated or unsaturated $C_6$-$C_{30}$, such as $C_{12}$-$C_{22}$ fatty acids. If they are unsaturated, these compounds can have one to three, conjugated or unconjugated, carbon-carbon double bonds.

The esters according to at least one embodiment can also be chosen from mono-, di-, tri- and tetra-esters, polyesters and mixtures thereof.

These esters can be for example oleate, laurate, palmitate, myristate, behenate, cocoate, stearate, linoleate, linolenate, caprate, arachidonates, or mixtures thereof such as the oleopalmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose.

Non-limiting mention can be made of the product sold under the name GLUCATE® DO by the company Amerchol, which is a dioleate of methylglucose.

Exemplary esters or of mixtures of esters of sugar of fatty acid include: the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the monolaurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Goldschmidt under the name TEGOSOFT® PSE.

The silicones usable in the composition of the present disclosure include but are not limited to volatile or nonvolatile, cyclic, linear or branched silicones, modified or not with organic groups, having a viscosity from $5\times10^{-6}$ to 2.5 $m^2/s$ at 25° C., such as from $1\times10^{-5}$ to 1 $m^2/s$.

The silicones usable according to the disclosure can be in the form of oils, waxes, resins or gums.

In some embodiments, the silicone is chosen from the polydialkylsiloxanes, such as the polydimethylsiloxanes (PDMS), and the organo-modified polysiloxanes having at least one functional group selected from the poly(alkoxylated) groups, the amine groups and the alkoxy groups.

The organopolysiloxanes are defined in more detail in the work of Walter NOLL "Chemistry and Technology of Silicones" (1968), Academic Press. They can be volatile or nonvolatile.

When they are volatile, the silicones are, for example, chosen from those with a boiling point between 60° C. and 260° C., and for further examples, chosen from:

Cyclic polydialkylsiloxanes having from 3 to 7, such as from 4 to 5 silicon atoms. It can be, for example, the octamethylcyclotetrasiloxane marketed under the name VOLATILE SILICONE® 7207 by UNION CARBIDE or SILBIONE® 70045 V2 by RHODIA, the decamethylcyclopentasiloxane marketed under the name VOLATILE SILICONE® 7158 by UNION CARBIDE, and SILBIONE® 70045 V5 by RHODIA, and mixtures thereof.

Non-limiting mentions can also be made of the cyclocopolymers of the dimethylsiloxanes/methylalkylsiloxane type, such as SILICONE VOLATILE® FZ 3109 marketed by the company UNION CARBIDE, of the formula IV:

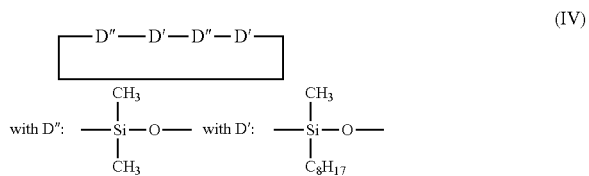

(IV)

Non-limiting mentions can further be made of the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy)bis-neopentane.

Other suitable volatile silicones include the linear volatile polydialkylsiloxanes having 2 to 9 silicon atoms and with a viscosity less than or equal to $5\times10^{-6}$ $m^2/s$ at 25° C. An example is decamethyltetrasiloxane, marketed under the name "SH 200" by the company TORAY SILICONE. Silicones included in this class are also described in the article published in Cosmetics and Toiletries, Vol. 91, January 76, p. 27-32—TODD BYERS "Volatile Silicone fluids for cosmetics".

Even further non-limiting mentions can be made of non-volatile polydialkylsiloxanes, gums and resins of polydialkylsiloxanes, polyorganosiloxanes modified with the aforementioned organofunctional groups, and mixtures thereof.

These silicones are, for example, chosen from the polydialkylsiloxanes, such as the polydimethylsiloxanes with trimethylsilyl end groups. The viscosity of the silicones is measured at 25° C. according to Standard Test Method for Kinematic Viscosity of Transparent and Opaque Liquids (and Calculation of Dynamic Viscosity)

Among these polydialkylsiloxanes, mention can be made of, non-exhaustively, the following commercial products: the SILBIONE® oils of series 47 and 70 047 or the MIRASIL® oils marketed by RHODIA, for example the oil 70 047 V 500 000; the oils of the MIRASIL® series marketed by the company RHODIA; the oils of the 200 series from the company DOW CORNING such as DC200, with a viscosity of 60 000 $mm^2/s$; the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name of dimethiconol (CTFA), such as the oils of the 48 series from the company RHODIA.

In this class of polydialkylsiloxanes, non-limiting mentions can be made of the products marketed under the names "ABIL WAX® 9800 and 9801" by the company GOLDSCHMIDT, which are polydialkyl ($C_1$-$C_{20}$) siloxanes.

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the polyisobutylenes, methylene chloride, pentane, dodecane, tridecane and mixtures thereof.

Products usable according to the disclosure are, for example, mixtures such as: mixtures formed from a chain end hydroxylated polydimethylsiloxane, or dimethiconol (CTFA) and a cyclic polydimethylsiloxane also called cyclomethicone (CTFA), such as the product Q2 1401 marketed by the company DOW CORNING; mixtures of a polydimethylsiloxane gum and a cyclic silicone such as the product SF 1214 Silicone Fluid from the company GENERAL ELECTRIC, said product being a gum SF corresponding to a dimethicone, having a number-average molecular weight of 500,000, dissolved in the oil SF 1202 Silicone Fluid corresponding to decamethylcyclopentasiloxane; mixtures of two PDMS of different viscosities, for example, of a PDMS gum and a PDMS oil, such as the product SF 1236 from the company GENERAL ELECTRIC. The product SF 1236 is a mixture of a gum SE 30 as defined above having a viscosity of 20 m²/s and an oil SF 96 with a viscosity of $5 \times 10^{-6}$ m²/s. This product, for example, has 15% of gum SE 30 and 85% of oil SF 96.

The organopolysiloxane resins usable according to the disclosure include but are not limited to crosslinked siloxane systems containing the units: $R_2SiO_{2/2}$, $R_3SiO_{1/2}$, $RSiO_{3/2}$ and $SiO_{4/2}$ Wherein R represents an alkyl having 1 to 16 carbon atoms. For example, R denotes a $C_1$-$C_4$ lower alkyl group such as methyl.

Among these resins, non-limiting mention can be made of the product marketed under the name "DOW CORNING® 593" or those marketed under the names "SILICONE FLUID SS 4230 and SS 4267" by the company GENERAL ELECTRIC, which are silicones of dimethyl/trimethyl siloxane structure.

Non-limiting mention can also be made of the resins of the trimethylsiloxysilicate type, such as those marketed under the names X22-4914, X21-5034 and X21-5037 by the company SHIN-ETSU.

The organomodified silicones usable according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, and polyalkyl-arylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from $1 \times 10^{-5}$ to $5 \times 10^2$ m²/s at 25° C.

Among these polyalkarylsiloxanes, non-limiting mentins can be made of the products marketed under the following names: the SILBIONE® oils of series 70 641 from RHODIA; the oils of the series RHODORSIL® 70 633 and 763 from RHODIA; the oil DOW CORNING® 556 COSMETIC GRADE FLUID from DOW CORNING; the silicones of the PK series from BAYER such as the product PK20; the silicones of the series PN, PH from BAYER such as the products PN1000 and PH1000; certain oils of the SF series from GENERAL ELECTRIC such as SF 1023, SF 1154, SF 1250, SF 1265.

Among the organomodified silicones, non-limiting mention can be made of the polyorganosiloxanes having: polyoxyethylene and/or polyoxypropylene groups optionally with $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the alkyl ($C_{12}$)-methicone copolyol marketed by the company DOW CORNING under the name Q2 5200; substituted or unsubstituted amine groups such as the products marketed under the name GP 4 Silicone Fluid and GP 7100 by the company GENESEE or the products marketed under the names Q2 8220 and DOW CORNING® 929 or 939 by the company DOW CORNING. The substituted amine groups are, for example, $C_1$-$C_4$ aminoalkyl groups; alkoxylated groups, such as the product marketed under the name "SILICONE COPOLYMER F-755" by SWS SILICONES and ABIL WAX® 2428, 2434 and 2440 by the company GOLDSCHMIDT.

In some embodiments, the at least one fatty substance is neither alkoxylated, nor glycerolated.

For example, the at least one fatty substance is chosen from compounds that are liquid or pasty at room temperature and at atmospheric pressure.

For further example, the at least one fatty substance is a compound that is liquid at a temperature of 25° C. and at atmospheric pressure.

The at least one fatty substance is, for example, chosen from the lower alkanes, fatty alcohols, esters of fatty acid, esters of fatty alcohol, and oils such as non-silicone mineral, vegetable and synthetic oils, the silicones.

According to at least one embodiment, the at least one fatty substance is chosen from liquid paraffin, polydecenes, liquid esters of fatty acids and of fatty alcohols, and mixtures thereof, for example, the at least one fatty substance of the composition according to the disclosure can be non-silicone.

In some embodiments, the at least one fatty substance is chosen from alkanes, hydrocarbons and silicones.

The composition according to the disclosure comprises at least one fatty substance other than a fatty acid, which is present in the composition in an amount of at least 10% by weight relative to the total weight of the composition. For example, the concentration of fatty substances is from about 10 to about 80% by weight, such as from about 15 to about 65% by weight, further such as from about 20 to about 55% by weight, based on the total weight of the composition.

Salts

The at least one salt of the present invention may be chosen from alkali earth metal salts and metal salts.

Suitable alkali earth metal salts may be chosen from Lithium, Sodium, Potassium, Magnesium, Calcium, Barium salts.

Suitable metal salts may be chosen from Manganese, Iron, Copper, Silver, Zinc, Aluminum salts.

In some embodiments, the salt is a mono- or a divalent metal. In some embodiments, the metal salt is a salt of a transition metal. In other embodiments, the metal salt is not a salt of an alkali earth metal.

The at least one salt of the present invention may be also chosen from salt compounds having organic counterions and salt compounds having polyatomic counterions such as an ammonium ion or such as a substituted ammonium ion.

In other embodiments, the at least one salt of the present invention may be chosen from silicates. Suitable silicates include, but are not limited to, metal silicates, organic silicates and polyatomic silicates.

Within the meaning of the present disclosure, "salt" is understood to include, but not limited to, the oxides and hydroxides of metals and the salts proper that can result from the action of an acid on a metal. In some embodiments, the at least one salt is not an oxide. In some embodiments, the at least one salt is not a hydroxide. Mention may be made, among the salts, of halides, such as chlorides, fluorides and iodides, sulfates, phosphates, lactates, acetates, glycinates, aspartates, nitrates, perchlorates, carbonates, hydrogen carbonates, silicates, borates and salts of carboxylic acids and polymeric complexes which can support said salts, and also their mixtures.

The salts of carboxylic acids which can be used in the disclosure also include salts of hydroxylated carboxylic acids, such as gluconate.

Mention may be made, as example of polymeric complexes which can support said salts, of manganese pyrrolidonecarboxylate.

One particularly preferred salt of the present invention is sodium sulfate.

It was surprisingly found that when the at least one salt is employed in the compositions of the present invention, less amounts of the alkaline agent and/or the oxidizing agent are necessary in order to achieve the desired degree of coloring of keratinous substrates. This would be more desirable since higher levels of the alkaline agent and/or oxidizing agent could result in more damage to the hair.

Moreover, when both the at least one salt and an oxidizing agent are present in the compositions of the present invention, peroxy compounds such as peroxyacids and peroxysalts, for example, peroxyborates, peroxycarbonates and peroxysulfates, may form in said compositions.

The at least one salt of the present invention can be present in an amount ranging from about 0.001% to about 40% by weight or from about 0.05% to about 30% by weight, or from about 0.1 to about 20%, or from about 1% to about 15%, based on the total weight of the composition.

Cationic Polymers

In at least one embodiment, the at least one cationic polymer included in the composition of the disclosure is not chosen from cationic associative polymers. In other words, these cationic polymers do not comprise in their structure a pendent or terminal hydrophobic chain, for example of alkyl or alkenyl type, containing from 10 to 30 carbon atoms.

The at least one cationic polymer of the composition according to the disclosure can be chosen from, for example:

(1) homopolymers and copolymers derived from acrylic or methacrylic esters or amides and comprising at least one unit chosen from units of formulae (V), (VI), (VII) and (VIII):

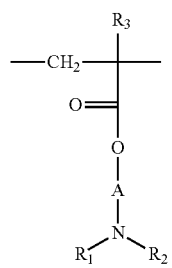

(V)

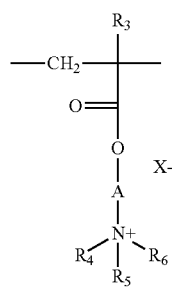

(VI)

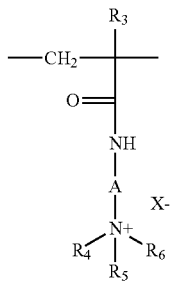

(VII)

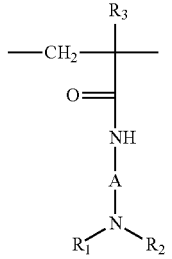

(VIII)

wherein:

$R_3$, which may be identical or different, denotes a hydrogen atom or a $CH_3$ radical;

A, which may be identical or different, represents a linear or branched $C_1$-$C_6$ and, for example, $C_2$-$C_3$ alkyl group or a $C_1$-$C_4$ hydroxyalkyl group;

$R_4$, $R_5$ and $R_6$, which may be identical or different, represent a $C_1$-$C_{18}$ alkyl group or a benzyl radical, such as a $C_1$-$C_6$ alkyl group;

$R_1$ and $R_2$, which may be identical or different, represent hydrogen or a $C_1$-$C_6$ alkyl group, for example methyl or ethyl;

$X^-$ denotes an anion derived from a mineral or organic acid, such as a methosulfate anion or a halide such as chloride or bromide.

The polymers of this family can also contain at least one unit derived from at least one comonomer which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among the polymers of this family, exemplary mention may be made of:

copolymers of acrylamide and of dimethylaminoethyl methacrylate quaternized with dimethyl sulfate or with a dimethyl halide, such as the product sold under the name HERCOFLOC by the company Hercules, the copolymers of acrylamide and of methacryloyloxyethyltrimethylammonium chloride described, for example, in EP 80 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or methacrylate copolymers, such as the products sold under the name GAFQUAT by the company ISP, for instance GAFQUAT 734 or GAFQUAT 755, or alternatively the products known as COPOLYMER 845, 958 and 937, dimethylaminoethyl methacrylate/vinylcaprolactam/vinylpyrrolidone terpolymers, such as the product sold under the name GAFFIX VC 713 by the company ISP, vinylpyrrolidone/methacrylamidopropyldimethylamine copolymers sold, for example, under the name STYLEZE CC 10 by ISP, quaternized vinylpyrrolidone/dimethylaminopropylmethacrylamide copolymers such as the product sold under the name GAFQUAT HS 100 by the company ISP, and crosslinked polymers of methacryloyloxy($C_1$-$C_4$)alkyltri($C_1$-$C_4$)alkylammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, such as methylenebisacrylamide. In at least one embodiment, a crosslinked acrylamide/methacryloyloxyethyltrimethylammonium chloride copolymer (20/80 by weight) in the form of a dispersion containing 50% by weight of the copolymer in mineral oil can be used. This dispersion is sold under the name SALCARE® SC 92 by the company Ciba. In some embodiments, a crosslinked methacryloyloxyethyltrimethylammonium chloride homopolymer containing about 50% by weight of the homopolymer in mineral oil or in a liquid ester can be used. These dispersions are sold under the names SALCARE® SC 95 and SALCARE® SC 96 by the company Ciba.

Other examples are cellulose ether derivatives comprising quaternary ammonium groups, such as the polymers sold under the names JR (JR 400, JR 125, JR 30M) or LR (LR 400, LR 30M) by the company Union Carbide Corporation.

(2) copolymers of cellulose or cellulose derivatives grafted with a water-soluble quaternary ammonium monomer, such as hydroxymethyl-, hydroxyethyl- or hydroxy-propylcelluloses grafted, for instance, with a methacryloylethyltrimethylammonium, methacrylamidopropyltrimethylammonium or dimethyldiallylammonium salt. These are sold under the name CELQUAT L 200 and CELQUAT H 100 by the company National Starch.

(3) non-cellulose cationic polysaccharides, such as guar gums containing trialkylammonium cationic groups. Such products are sold, for example, under the trade names JAGUAR C13S, JAGUAR C15, JAGUAR C17 and JAGUAR C162 by the company Meyhall.

(4) polymers of piperazinyl units and of divalent alkylene or hydroxyalkylene radicals.

(5) water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 to 0.35 mol per amine group of the polyamino amide; these polyamino amides can be alkylated or, if they contain at least one tertiary amine function, they can be quaternized. Exemplary mention may be made of the adipic acid/dimethylaminohydroxypropyl/diethylenetriamine polymers sold under the name CARTARETINE F, F4 or F8 by the company Sandoz.

(6) the polymers obtained by reaction of at least one polyalkylene polyamine containing two primary amine groups and at least one secondary amine group with a dicarboxylic acid chosen from diglycolic acid and saturated $C_3$-$C_8$ aliphatic dicarboxylic acids. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Polymers of this type are sold, for example, under the name HERCOSETT 57, PD 170 or DELSETTE 101 by the company Hercules.

(7) cyclopolymers of alkyldiallylamine and of dialkyldiallylammonium, such as the homopolymers or copolymers containing, as main constituent of the chain, at least one unit corresponding to formula (IX) or (X):

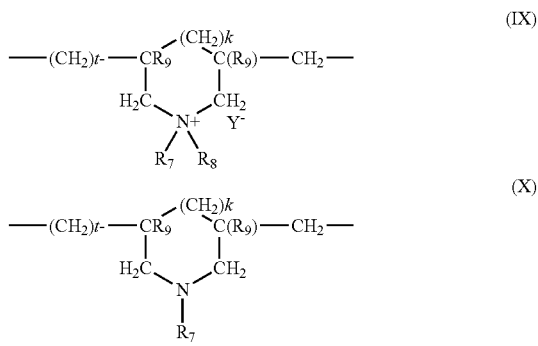

wherein formulae k and t are equal to 0 or 1, the sum k+t being equal to 1; $R_9$ denotes a hydrogen atom or a methyl radical; $R_7$ and $R_8$, independently of each other, denote a $C_1$-$C_8$ alkyl group, a hydroxyalkyl group in which the alkyl group is $C_1$-$C_5$, an amidoalkyl group in which the alkyl is $C_1$-$C_4$; or $R_7$ and $R_8$ denote, together with the nitrogen atom to which they are attached, a heterocyclic group such as piperidyl or morpholinyl; in at least one embodiment $R_7$ and $R_8$, independently of each other, denote a $C_1$-$C_4$ alkyl group; $Y^-$ is an organic or mineral anion such as bromide, chloride, acetate, borate, citrate, tartrate, bisulfate, bisulfite, sulfate or phosphate.

Among the polymers defined above, exemplary mention may be made of the dimethyldiallylammonium chloride homopolymer sold under the name MERQUAT 100 and MERQUAT 280 by the company Nalco (and its homologues of low weight-average molecular mass) and the copolymers of diallyldimethylammonium chloride and of acrylamide, sold under the name MERQUAT 550.

(8) quaternary diammonium polymers containing repeating units of formula (XI):

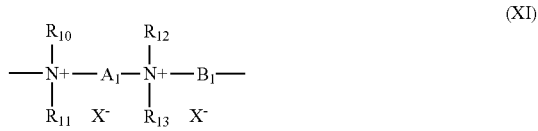

wherein:

$R_{10}$, $R_{11}$, $R_{12}$ and $R_{13}$, which may be identical or different, represent $C_1$-$C_6$ aliphatic, alicyclic or arylaliphatic radicals or hydroxyalkylaliphatic radicals wherein the alkyl radical is $C_1$-$C_4$, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D wherein $R_{14}$ is an alkylene and D is a quaternary ammonium group;

$A_1$ and $B_1$ represent $C_2$-$C_6$ polymethylene groups which are linear or branched, saturated or unsaturated, and which optionally contain, linked to or intercalated in the main chain, at least one aromatic ring or at least one atom chosen from oxygen and sulfur atom or at least one group chosen from sulfoxide, sulfone, disulfide, amino, alkylamino, hydroxyl, quaternary ammonium, ureido, amide and ester groups, and $X^-$ denotes an anion derived from a mineral or organic acid;

$A_1$, $R_{10}$ and $R_{12}$ can form, with the two nitrogen atoms to which they are attached, a piperazine ring;

and wherein, if $A_1$ denotes a linear or branched, saturated or unsaturated alkylene or hydroxyalkylene radical, $B_1$ can also denote a group —$(CH_2)_n$—CO-D—OC—$(CH_2)_n$— wherein n is a number ranging from 1 to 6, and D is chosen from:

a) a glycol residue of formula: —O—Z—O—, where Z denotes a linear or branched hydrocarbon-based radical or a group corresponding to one of the following formulae: —$(CH_2$—$CH_2$—O$)_x$—$CH_2$—$CH_2$—; or —[$CH_2$—$CH(CH_3)$—O$]_y$—$CH_2$—$CH(CH_3)$—, where x and y denote an integer ranging from 1 to 4, representing a defined and unique degree of polymerization or any number ranging from 1 to 4 representing an average degree of polymerization;

b) a bis-secondary diamine residue such as a piperazine derivative;

c) a bis-primary diamine residue of formula: —NH—Y—NH—, wherein Y denotes a linear or branched hydrocarbon-based radical, or alternatively the radical —$CH_2$—$CH_2$—S—S—$CH_2$—$CH_2$—; and d) an ureylene group of formula: —NH—CO—NH—.

In at least one embodiment, $X^-$ is an anion such as chloride or bromide.

These polymers, for example, have a number-average molecular mass ranging from 1000 to 100,000.

In some embodiments, polymers are used that consist of repeating units corresponding to formula (XII):

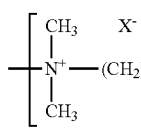

wherein $R_{10}$, $R_{11}$, $R_{12}$ and $R_{13}$, which may be identical or different, denote a $C_1$-$C_4$ alkyl or hydroxyalkyl radical, n and p are integers ranging from 2 to 6, and $X^-$ is an anion derived from a mineral or organic acid.

In at least one embodiment, the at least one cationic polymer corresponding to this family comprise repeating units of formulae (W) and (U):

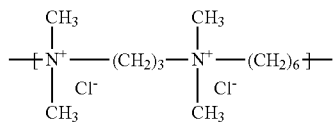

for example those whose molecular weight, determined by gel permeation chromatography, ranges from 9,500 to 9,900;

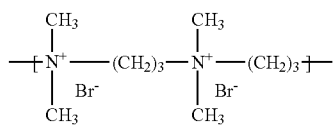

for instance those whose molecular weight, determined by gel permeation chromatography, is 1200.

(9) polyquaternary ammonium polymers consisting of repeating units of formula (XIII):

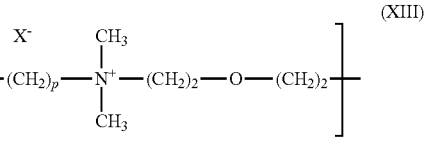

wherein p denotes an integer ranging from 1 to 6, D may be zero or may represent a group —$(CH_2)_r$—CO— wherein r denotes a number ranging from 1 to 6, and $X^-$ is an anion.

Such polymers may be prepared according to the processes described in U.S. Pat. Nos. 4,157,388, 4,702,906 and 4,719,282. They are described, for example, in patent application EP 122 324.

Among these polymers, examples that may be mentioned include the products MIRAPOL A 15, MIRAPOL AD1, MIRAPOL AZ1 and MIRAPOL 175 sold by the company Miranol.

(10) quaternary polymers of vinylpyrrolidone and of vinylimidazole, for instance the products sold under the names LUVIQUAT FC 905, FC 550 and FC 370 by the company BASF.

(11) vinylamide homopolymers or copolymers, such as partially hydrolysed vinylamide homopolymers such as poly(vinylamine/vinylamide)s.

(12) cationic polyurethane derivatives, for example those of elastic nature formed from the reaction:

(a1) of at least one cationic unit resulting from at least one tertiary or quaternary amine bearing at least two reactive functions containing labile hydrogen, (a2) of at least one mixture of at least two different nonionic units bearing at least two reactive functions containing labile hydrogen, for instance chosen from hydroxyl groups, primary or secondary amine groups, and thiol groups, and (b) of at least one compound comprising at least two isocyanate functions.

(13) Other cationic polymers that may be used in the context of the disclosure include, for example, cationic proteins or cationic protein hydrolysates, polyalkyleneimines, such as polyethyleneimines, polymers containing vinylpyridine or vinylpyridinium units, and chitin derivatives.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

The cationic polymer is generally present in an amount of from greater than 0% to about 15%, preferably from about 0.5 to about 10% by weight, and more preferably from about 1 to about 5% by weight, based on the total weight of the composition.

Oxidizing Agent

The compositions of the present disclosure may require an oxidizing agent when the colorant comprises an oxidative dye. Oxidizing agents are used in an amount sufficient for the oxidative dye to develop a color. The oxidizing agents may be, for example, peroxide, a persulfate, a perborate, a percarbonate, alkali metal bromates, ferricyanides or a mixture thereof. Oxidizing agents that may also be used include at least one redox enzyme such as laccases, peroxidases, and 2-electron oxidoreductases, such as uricase, where appropriate in the presence of their respective donor or co-factor.

In one embodiment, the oxidizing agent is hydrogen peroxide present in an aqueous solution whose titre may range from 1 to 40 volumes, such as from 5 to 40 volumes.

In another embodiment, the oxidizing agent is a persulfate and/or a monopersulfate such as, for example, potassium persulfate, sodium persulfate, ammonium persulfate, as well as mixtures thereof. In one embodiment the oxidizing agents in the present disclosure are selected from hydrogen peroxide, potassium persulfate, sodium persulfate and mixtures thereof.

Typically, the oxidizing agent is provided in the form of a developer composition.

In one embodiment, the oxidizing agent is present in an amount of at least 1% by weight, based on the total weight of the developer composition.

In another embodiment, the oxidizing agent is present in an amount ranging of from greater than 0% to about 40% by weight, or from about 0.01% to about 30% by weight, or from about 0.1% to about 20% by weight, or from about 1% to about 15% by weight, based on the total weight of the developer composition.

Developer Composition

The developer composition may be in the form of a powder, gel, liquid, foam, lotion, cream, mousse, and emulsion.

In one particular embodiment, the developer composition is aqueous or is in the form of an emulsion.

In another embodiment, the developer composition is substantially anhydrous. The term "substantially anhydrous" means that the developer composition is either completely free of water or contains no appreciable amount of water, for example, no more than 5% by weight, or no more than 2% by weight, or no more than 1% by weight, based on the weight of the developer composition. It should be noted that this refers for example to bound water, such as the water of crystallization of the salts or traces of water absorbed by the raw materials used in the preparation of the compositions according to the disclosure.

The developer composition can contain at least one solvent, chosen from water, organic solvents, and mixtures thereof.

When the developer composition is substantially anhydrous, the developer composition may comprise at least one solvent chosen from organic solvents.

Suitable organic solvents for use in the developer composition include ethanol, isopropyl alcohol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The at least one solvent may, for example, be present in an amount ranging from about 0.5% to about 70% by weight, such as from about 2% to about 60% by weight, preferably from about 5% to about 50% by weight, relative to the total weight of the developer composition.

The pH of the developer composition can range from 2 to 12, such as from 6 to 11, and it may be adjusted to the desired value using acidifying/alkalizing agents that are well known in the art.

Cosmetically Acceptable Medium

The ready-to-use composition according to the disclosure can be in various forms, such as in the form of liquids, creams, gels, lotions or paste.

The ready-to-use composition can comprise other compounds constituting the cosmetically acceptable medium. This cosmetically acceptable medium comprises water or a mixture of water and at least one cosmetically acceptable organic solvent.

As examples of organic solvents, non-limiting mentions can be made of alcohols such as ethyl alcohol, isopropyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Additive

The ready-to-use composition according to the disclosure can also comprise at least one additive used conventionally in compositions for application onto hair.

"Additive" means a substance that is added, different from the compounds already mentioned.

As examples of additives that can be used, non-limiting mentions can be made of surfactants, antioxidants or reducing agents, penetrating agents, sequestering agents, perfumes, buffers, dispersants, conditioners, such as for example volatile or non-volatile, modified or unmodified silicones, film-forming agents, ceramides, preservatives, opacifiers, and antistatic agents.

Preparation and Application of the Ready-to-Use Composition

According one embodiment of the invention, the ready-to-use compositions according to the disclosure can be prepared from a dye composition comprising at least one direct dye as defined previously, with or without any developer composition.

According to another embodiment of the invention the ready-to-use compositions according to the disclosure can result from mixing two units, including a first unit of an oxidative dye containing composition as defined previously and a second unit of a developer composition as defined above, or vice versa.

According to yet another embodiment of the invention, a pre-treatment composition containing at least one salt may be provided and applied onto the keratinous substrates prior to the application of the ready-to-use composition.

It has been surprisingly discovered that the composition of the present invention enables acceptable levels of dye to be deposited onto keratinous substrates utilizing lower amounts of dye compared to conventional dyeing compositions.

Yet another surprising discovery is that in the event conventional amounts of dye are employed, the dyeing process may be completed in less time such as 20 minutes or 15 minutes or 10 minutes, thereby causing less damage to the keratinous substrates.

In the event that conventional levels of dye are employed, coupled with conventional dyeing times, significantly larger color deposit onto the keratinous substrate may be achieved.

Finally, the inventive composition contains large amounts of water, e.g., higher than 60%, or 80% by weight, which advantageously lowers the cost of production.

According to another embodiment of the invention, a kit for dyeing keratinous substrates is provided, comprising:

a first unit containing in a cosmetically acceptable medium: at least one phospholipid; at least one nonionic surfactant; at least one compound chosen from an alkyl ether carboxylic acid, an alkyl ether carboxylate, a fatty acid having from about 6 to about 40 carbon atoms, and mixtures thereof; and at least one dye chosen from oxidation dye precursors and direct dyes; optionally, at least one thickening agent; optionally, at least one alkaline agent; optionally, at least one fatty substance other than a fatty acid; and optionally, at least one salt; and a second unit comprising at least one oxidizing agent and optionally, at least one fatty substance other than a fatty acid.

According to yet another embodiment of the invention, the kit further comprises a third unit containing at least one salt in a cosmetically acceptable medium.

The invention will be further clarified by the following examples, which are intended to be illustrative of the invention, but not limiting thereof.

EXAMPLES

Example 1

Low pH Blue Binary Color Deposit Study

A test swatch of IHIP 90% gray hair (1 cm width, 15 cm length) was dyed with 20 g of the mixture of the below dye composition mixed 1:1 with L'Oreal Majicreme™ 20 volume developer. The pH of the final mixture was adjusted to 6.5 using NaOH.

| Ingredient | Example 1 |
| --- | --- |
| DI Water | Q.S. |
| Lecithin | 1.0% |
| PPG-5 Ceteth-20 | 15.0% |
| Laureth-11 Carboxylic Acid | 0.9% |
| Mineral Oil | 1.0% |
| N,N-Bis (2-hydroxyethyl) p-phenylenediamine sulfate | 1.47% |
| 2,4-Diaminophenoxyethanol HCl | 1.205% |

A control swatch was dyed with the mixture of Redken Shades EQ™ clear, containing the same dyes at same levels as above, mixed 1:1 with Redken Shades EQ™ Processing solution. The pH of the final mixture was adjusted to 6.5 using NaOH.

Both swatches were processed for 20 minutes at RT, rinsed for 1 minute (80 gph, 32° C.), and dried. L*a*b* values were measured before and after coloring using Konica Minolta Spectrophotometer.

The final ΔL value measurements for the control and test swatches were −54.32 and −64.47, respectively. More negative ΔL value indicates darker color. The color intensity difference is also visually significant. Therefore the inventive formula deposits greater amounts of color on the hair than the control in the 20 minutes processes.

Example 2

High pH Blue Binary Color Deposit Study

A test swatch of IHIP 90% gray hair (1 cm width, 15 cm length) was dyed with 20 g of the mixture of the below dye composition mixed 1:1 with L'Oreal Majicreme™ 20 volume developer. The pH of the final mixture was adjusted to 9.5 using NaOH.

| Ingredient | Example 2 |
| --- | --- |
| DI Water | Q.S. |
| Lecithin | 1.0% |
| PPG-5 Ceteth-20 | 15.0% |
| Laureth-11 Carboxylic Acid | 0.9% |
| Mineral Oil | 1.0% |
| N,N-Bis (2-hydroxyethyl) p-phenylenediamine sulfate | 1.47% |
| 2,4-Diaminophenoxyethanol HCl | 1.205% |

A control swatch was dyed with the mixture of L'Oreal Preference™ base containing the same dyes at same levels as above, mixed 1:1 with L'Oreal Preference™ 20 volume developer. The pH of the final mixture was adjusted to 9.5 using NaOH.

Both swatches were processed for 20 minutes at RT, rinsed for 1 minute (80 gph, 32° C.), and dried. L*a*b* values were measured before and after coloring using Konica Minolta Spectrophotometer.

The final ΔL value measurements for the control and test swatches were −54.32 and −64.56, respectively. More negative ΔL value indicates darker color. The color intensity difference is also visually significant. Therefore the inventive formula deposits greater amounts of color on the hair than the control in the 20 minutes processes.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

What is claimed is:

1. A ready-to-use aqueous composition for dyeing keratinous substrates comprising, in a cosmetically acceptable medium,
   a) at least one phospholipid;
   b) at least one nonionic surfactant;
   c) at least one compound chosen from an alkyl ether carboxylic acid, an alkyl ether carboxylate, a fatty acid having from about 6 to about 40 carbon atoms, and mixtures thereof;
   d) at least one dye chosen from oxidation dye precursors and direct dyes;
   e) optionally, at least one thickening agent;
   f) optionally, at least one alkaline agent;
   g) optionally, at least one fatty substance other than a fatty acid;
   h) optionally, at least one salt; and
   i) at least one oxidizing agent.

2. The composition of claim 1 wherein (a) is lecithin.

3. The composition of claim 1 wherein (a) is linoleamidopropyl PG-dimonium chloride phosphate.

4. The composition of claim 1 wherein (a) is present in an amount of from greater than 0 to about 30% by weight, based on the weight of the composition.

5. The composition of claim 1 wherein (a) is present in an amount of from about 0.1 to about 5% by weight, based on the weight of the composition.

6. The composition of claim 1 wherein (b) has an HLB of at least about 8.

7. The composition of claim 1 wherein (b) is present in an amount of from greater than 0 to about 70% by weight, based on the weight of the composition.

8. The composition of claim 1 wherein (b) is present in an amount of from about 1 to about 30% by weight, based on the weight of the composition.

9. The composition of claim 1 wherein (c) is an alkyl ether carboxylic acid.

10. The composition of claim 1 wherein (c) is a laureth-5 carboxylic acid.

11. The composition of claim 1 wherein (c) is an oleth-10 carboxylic acid.

12. The composition of claim 1 wherein (c) is a laureth-11 carboxylic acid.

13. The composition of claim 1 wherein (c) is a fatty acid having from about 6 to about 40 carbon atoms.

14. The composition of claim 1 wherein (c) is Oleic Acid.

15. The composition of claim 1 wherein (c) is Stearic Acid.

16. The composition of claim 1 wherein (c) is present in an amount of from greater than 0 to about 40% by weight, based on the weight of the composition.

17. The composition of claim 1 wherein (c) is present in an amount of from about 0.5 to about 20% by weight by weight, based on the weight of the composition.

18. The composition of claim 1, wherein (d) is chosen from oxidation bases and couplers, and mixtures thereof.

19. The composition of claim 1, wherein (d) is chosen from ortho- and para-phenylenediamine oxidation bases, double bases, ortho- and para-aminophenols, heterocyclic bases, as well as salts of addition of these compounds with an acid and meta-aminophenol, meta-phenylenediamine, meta-diphenol, naphthol couplers, heterocyclic couplers and acid salts thereof.

20. The composition of claim 1, wherein (d) is chosen from aminophenols and meta-phenylenediamines.

21. The composition of claim 1, wherein (d) is chosen from direct dyes.

22. The composition of claim 1, wherein (e) is chosen from a polymeric thickener and a non-polymeric thickener and is present in an amount of from about 0.01 to about 10% by weight.

23. The composition of claim 1, wherein (e) is present in an amount of from about 0.5 to about 5% by weight.

24. The composition of claim 1, wherein (f) is chosen from organic amines, organic amine salts, ammonium salts, and inorganic bases and is present from about 0.001% to about 30% by weight.

25. The composition of claim 1, wherein (f) is present in an amount of from about 0.1 to about 15% by weight.

26. The composition of claim 1, wherein (g) is chosen from lower alkanes, fatty alcohols, esters of fatty acids, esters of fatty alcohol, non-silicone oils, non-silicone waxes and silicones and is present in an amount of from about 10 to about 80% by weight.

27. The composition of claim 1, wherein (g) is non-silicone.

28. The composition of claim 1, wherein (g) is present in an amount of from about 20 to about 55% by weight.

29. The composition of claim 1, wherein (h) is chosen from salt compounds of halides, sulfates, phosphates, lactates, acetates, glycinates, aspartates, nitrates, perchlorates, carbonates, hydrogen carbonates, silicates, borates, and carboxylic acids and is present in an amount of from about 0.001% to about 40% by weight.

30. The composition of claim 1, wherein (h) is present in an amount of from about 0.1 to about 20% by weight.

31. The composition of claim 1, wherein (h) is sodium sulfate.

32. The composition of claim 1, wherein (i) is chosen from peroxides, bromates of alkali metals, ferricyanides of alkali metals, peroxygenated salts, oxidoreduction enzymes, and oxygen in air and is present in an amount of from about 0.001% to about 40% by weight.

33. The composition of claim 1, wherein (i) is present in an amount of from about 0.1 to about 20% by weight.

34. The composition of claim 1, wherein (i) is hydrogen peroxide.

35. The composition of claim 1 wherein the composition further comprises a cationic polymer and is present in an amount of from greater than 0% to about 15% by weight.

36. The composition of claim 1 wherein the composition further comprises a cationic polymer and is present in an amount of from about 1% to about 5% by weight.

37. The composition of claim 1 is substantially free of ammonia.

38. The composition of claim 1 wherein the pH of the composition is at least 9.

39. The composition of claim 1 wherein the pH of the composition is from about 9 to about 11.

40. The composition of claim 1 wherein the pH of the composition is less than or equal to 7.

41. The composition of claim 1 wherein the pH of the composition is from about 6 to about 7.

42. A method of dyeing keratinous substrates, comprising applying onto the keratinous substrates a ready-to-use aqueous composition containing, in a cosmetically acceptable medium,
   a) at least one phospholipid;
   b) at least one nonionic surfactant;

c) at least one compound chosen from an alkyl ether carboxylic acid, an alkyl ether carboxylate, a fatty acid having from about 6 to about 40 carbon atoms, and mixtures thereof;
d) at least one dye chosen from oxidation dye precursors and direct dyes;
e) optionally, at least one thickening agent;
f) optionally, at least one alkaline agent;
g) optionally, at least one fatty substance other than a fatty acid;
h) optionally, at least one salt; and
i) at least one oxidizing agent.

43. The method of claim 42 further comprising:
a) providing a pre-treatment composition containing at least one salt; and
b) applying the pre-treatment composition prior to the application of the ready-to-use aqueous composition, wherein the pretreatment composition comprises at least one salt in a cosmetically acceptable medium.

44. A ready-to-use aqueous composition for the oxidative dyeing of keratinous substrates comprising, in a cosmetically acceptable medium,
a) from about 0.1% to about 5% by weight at least one phospholipid;
b) from about 1% to about 30% by weight at least one nonionic surfactant;
c) from about 0.5 to about 20% by weight at least one compound chosen from an alkyl ether carboxylic acid, an alkyl ether carboxylate, a fatty acid having from about 6 to about 40 carbon atoms, and mixtures thereof;
d) at least one oxidative dye chosen from oxidation bases and couplers;
e) optionally, at least one thickening agent;
f) from about 0.1 to about 15% by weight of at least one alkaline agent;
g) at least 10% by weight of at least one fatty substance other than a fatty acid;
h) optionally, at least one salt; and
i) from about 0.1 to about 20% by weight of at least one oxidizing agent.

45. A kit for dyeing keratinous substrates, comprising:
1) a first unit containing, in a cosmetically acceptable medium:
a) at least one phospholipid;
b) at least one nonionic surfactant;
c) at least one compound chosen from an alkyl ether carboxylic acid, an alkyl ether carboxylate, a fatty acid having from about 6 to about 40 carbon atoms, and mixtures thereof;
d) at least one oxidative dye chosen from oxidation bases and couplers; and
e) optionally, at least one thickening agent;
f) optionally, at least one alkaline agent;
g) optionally, at least one fatty substance other than a fatty acid; and
h) optionally, at least one salt; and
2) a second unit comprising at least one oxidizing agent and optionally, at least one fatty substance other than a fatty acid.

46. A kit for dyeing keratinous substrates, comprising:
1) a first unit containing, in a cosmetically acceptable medium:
a) at least one phospholipid;
b) at least one nonionic surfactant;
c) at least one compound chosen from an alkyl ether carboxylic acid, an alkyl ether carboxylate, a fatty acid having from about 6 to about 40 carbon atoms, and mixtures thereof;
d) at least one oxidative dye chosen from oxidation bases and couplers; and
e) optionally, at least one thickening agent;
f) optionally, at least one alkaline agent;
g) optionally, at least one fatty substance other than a fatty acid; and
h) optionally, at least one salt;
2) a second unit comprising at least one oxidizing agent and optionally, at least one fatty substance other than a fatty acid; and
3) a third unit comprising at least one salt in a cosmetically acceptable medium.

* * * * *